United States Patent [19]
Van Der Puy et al.

[11] Patent Number: 5,532,419
[45] Date of Patent: Jul. 2, 1996

[54] PROCESSES FOR THE PREPARATION OF FLUORINATED OLEFINS AND HYDROFLUOROCARBONS USING FLUORINATED OLEFIN

[75] Inventors: Michael Van Der Puy, Cheektowaga; G. V. Bindu Madhavan, Amherst; Alagappan Thenappan, Cheektowaga; Hsueh S. Tung, Getzville, all of N.Y.

[73] Assignee: AlliedSignal Inc., Morris County, N.J.

[21] Appl. No.: 528,846

[22] Filed: Sep. 15, 1995

Related U.S. Application Data

[62] Division of Ser. No. 412,476, Mar. 28, 1995, Pat. No. 5,481,050, which is a division of Ser. No. 242,899, May 16, 1994, Pat. No. 5,446,217.

[51] Int. Cl.$^6$ .......... C07C 17/097; C07C 19/01; C07C 19/08; C07C 19/10
[52] U.S. Cl. .......... 570/167; 570/135; 570/156
[58] Field of Search .......... 570/167

[56] References Cited

U.S. PATENT DOCUMENTS

| | | | |
|---|---|---|---|
| 2,005,708 | 6/1935 | Davdt et al. | 570/167 |
| 2,500,218 | 3/1950 | Towne et al. | 570/167 |
| 2,700,688 | 1/1955 | Crane et al. | 570/157 |
| 2,862,036 | 11/1958 | Baranauckas et al. | 570/167 |
| 2,889,379 | 6/1959 | Ruh et al. | |
| 3,631,115 | 12/1971 | Nakagawa et al. | 570/172 |
| 3,862,978 | 1/1975 | Decker et al. | 570/172 |
| 4,058,573 | 11/1977 | Knell | |
| 4,078,007 | 3/1978 | Ferstandig | |
| 4,110,407 | 8/1978 | Anello et al. | 570/157 |
| 4,465,786 | 8/1984 | Zimmer et al. | |
| 4,798,818 | 1/1989 | Baizer et al. | |
| 5,017,718 | 5/1991 | Ojima et al. | 570/172 |
| 5,254,773 | 10/1993 | Wright | 570/172 |

FOREIGN PATENT DOCUMENTS

| | | | |
|---|---|---|---|
| 697280 | 11/1964 | Canada | 570/156 |
| 2627180 | 8/1989 | France | |
| 1140928 | 12/1962 | Germany | |
| 2120327 | 6/1987 | Japan | 570/172 |
| 623227 | 5/1949 | United Kingdom | 570/167 |
| 982498 | 6/1963 | United Kingdom | 570/158 |

OTHER PUBLICATIONS

Brace et al., "Effect of a Perfluoroalkyl Group on the Elimination and Substitution Reactions of Two Homologous Series of Perfluoroalkyl–Substituted Iodoalkanes," 49, *J. Org. Chem.*, 2361 (1984).

Henne et al., "Influence of a $CF_3$ Group on an Adjacent Double Bond," 72 *J. Am. Chem. Soc.*, 3369 (1950).

Chem. Abstr. 1992, 117:69439b.

*Primary Examiner*—Joseph E. Evans
*Attorney, Agent, or Firm*—Jay P. Friedenson; Colleen Szuch

[57] ABSTRACT

The invention relates to a cost effective and convenient process for the manufacture of fluorinated olefins of the formula $RCF_2CH{=}CH_2$ where R is $C_xCl_yF_z$ and $y+z=2x+1$. The invention is also directed to a practical process for converting these olefins to hydrofluorocarbons via the catalyzed fluorination with hydrogen fluoride. Hydrofluorocarbons produced via this process have application as solvents among other uses.

10 Claims, No Drawings

PROCESSES FOR THE PREPARATION OF FLUORINATED OLEFINS AND HYDROFLUOROCARBONS USING FLUORINATED OLEFIN

This application is a division of Ser. No. 08/412,476 filed on Mar. 28, 1995, now U.S. Pat. No. 5,481,050, which is a division of Ser. No. 08/242,899 filed on May 16, 1994 now U.S. Pat. No. 5,446,217.

BACKGROUND OF THE INVENTION

The invention relates to a cost effective and convenient process for the manufacture of fluorinated olefins of the formula $RCF_2CH=CH_2$ where R is $C_xCl_yF_z$ and $y+z=2x+1$ which may be used as starting materials for the manufacture of hydrofluorocarbons. The invention is also directed to a practical process for converting these olefins to hydrofluorocarbons via catalyzed fluorination with hydrogen fluoride. The hydrofluorocarbons produced via this process have utility, among other things, as solvents.

Traditionally, chlorofluorocarbons (CFCs) like trichlorofluoromethane (CFC-11), dichlorodifluoromethane (CFC-12) and 1,1,2-trichloro-1,2,2-trifluoroethane (CFC-113) have been used as solvents, refrigerants, blowing agents and diluents for gaseous sterilization. These materials, however, are suspect since they are believed to contribute to the stratospheric ozone depletion problem. The fluorocarbon industry has therefore focused its attention on developing stratospherically safer alternatives to these materials. Hydrofluorocarbons (HFC's) like $CF_3CF_2CH_2CH_2F$ (HFC-356mcfq), which has been identified as a solvent, are candidate replacement materials since they have no ozone depletion potential, contribute negligibly to global warming and offer substantially the same performance advantages such as nonflammability. As a result, methods for the manufacture of these materials need to be developed.

A few methods for the manufacture of compounds of the formula $RfCH=CH_2$ where Rf is $C_nF_{2n+1}$ are known in the art. See, e.g., U.S. Pat. No. 4,058,573 and Brace et. al., Effect of a perfluoroalkyl group on the elimination and substitution reactions of two homologous series of perfluoroalkyl-substituted iodoalkanes, 49 J. Org. Chem., 2361 (1984). These references disclose the addition of a perfluoroalkyl iodide to ethylene to yield $RfCH_2CH_2I$, followed by dehydroiodination to provide the olefin, $RfCH=CH_2$. This method is convenient only for the preparation of small quantities of materials because of the prohibitively high cost of the perfluoroalkyl iodide.

U.S. Pat. Nos. 2,889,379 ('379 patent), 4,798,818 ('818 patent), and 4,465,786 ('786 patent) disclose the preparation of $CF_3CH=CH_2$ by the catalyzed vapor phase fluorination of various halogen-containing $C_3$ compounds such as $CCl_3CH_2CH_2Cl$. These references however, do not teach or suggest that higher molecular weight homologs can be prepared by this method.

The halogen exchange in the precursors to the fluorinated olefins of our invention is dissimilar to the halogen exchange reported in these references. That is, the references are replacing the chlorine in a —$CCl_3$ group with fluorine while we are replacing the chlorine in a —$CF_2CCl_2CH_2$ group with fluorine. U.S. Pat. No. 4,078,007 discloses the liquid phase antimony pentachloride catalyzed fluorination with HF of $CCl_3CH_2CH_2Cl$ (the same compounds used in the '379, '818 and '786 patents) to provide $CF_3CH_2CH_2Cl$ at reaction temperatures of about 85° C. However, the liquid phase antimony pentachloride catalyzed fluorination with HF of $CF_3CCl_2CH_2CH_2Cl$ (a precursor of the fluorinated olefins of our invention) even at substantially higher reaction temperatures failed to result in even modest fluorination. That is, of the product recovered, 97% was starting material. See Comparative Examples 1 and 2.

As far as methods for the synthesis of HFC's from fluorinated olefins is concerned, Henne et al., Influence of a $CF_3$ group on an adjacent double bond, 72 J. Am. Chem. Soc., 3369 (1950) report that the $CF_3$ group in $CF_3CH=CH_2$ adversely affects the rate of addition of acids, HX where X is Br or Cl, to the carbon-carbon double bond. That is, Lewis acid catalysts and elevated temperatures are required to force these additions and even then modest yields and/or conversions may be obtained.

We have discovered: 1) a novel method for the production of fluorinated olefins and 2) a novel method for the manufacture of various HFC's using these fluorinated olefins as starting materials which overcome the drawbacks of the prior art processes discussed above.

DESCRIPTION OF THE INVENTION

This invention relates, in part, to a cost effective and convenient process for the manufacture of compounds of the formula $RCF_2CH=CH_2$ where R is $C_xCl_yF_z$ and $y+z=2x+1$. Preferably, the invention relates to preparation of compounds of the formula $RCF_2CH=CH_2$ where R is $C_xCl_yF_z$ and where $x \leq 4$ and $y \leq 2$ such as $CF_3CF_2CH=CH_2$, $CF_3CF_2CF_2CH=CH_2$, and $(CF_3)CFCF_2CH=CH_2$ comprising:

a) reacting a compound of the formula $RCX_aF_b$; where $R=C_mX_nF_o$, $m \leq 4$, $n \leq 2$, $m+o=2m+1$, X=Cl or Br, $a=2-3$, and $b=0-1$, with ethylene in the presence of an addition catalyst and a solvent under conditions sufficient to produce a compound of the formula $RCX_{a-1}F_bCH_2CH_2X$ where X=Cl or Br, $a=2-3$, $b=0-1$ and $a+b=3$;

b) reacting a compound of the formula $RCX_{a-1}F_bCH_2CH_2X$ where X=Cl or Br, $a=2-3$, $b=0-1$ and $a+b=3r$ with hydrogen fluoride in the presence of a fluorination catalyst under conditions sufficient to produce a compound of the formula $RCF_2CH=CH_2$ where R is $C_xCl_yF_z$ where $y+z=2x+1$; and c) recovering a compound of the formula $RCF_2CH=CH_2$ where R is $C_xCl_yF_z$ and $y+z=2x+1$.

The starting material for the addition reaction, i.e., ethylene and compounds of the formula $RCX_aF_b$; where $R=C_mX_nF_o$, $m \leq 4$, $n \leq 2$, $m+o=2m+1$, X=Cl or Br, $a=2-3$, $b=0-1$, and $a+b=3$ are commercially available from AlliedSignal Inc. or other domestic chemical manufacturers. Alternately, they may be synthesized by methods well known in the art. Suitable halogenated starting materials include, but are not limited to: $CF_3CCl_3$, $CF_2ClCFCl_2$, $CF_3CF_2CCl_3$, $ClCF_2CF_2CCl_3$, $CCl_3CF_2CCl_3$, $CF_2BrCF_2CFBr_2$, $CF_3CCl_2CF_2CCl_3$, $(CF_3)(CF_2Cl)CFCCl_3$, $(CF_3)_2CFCCl_3$, $ClCF_2CFClCF_2CFCl_2$. Preferred starting materials include: $CF_3CCl_3$, $CF_2ClCFCl_2$, $ClCF_2CF_2CCl_3$ and $CCl_3CF_2CCl_3$.

Any commercially available catalyst known in the art to be useful in catalyzing the addition of halocarbons to olefins may be employed. Suitable addition catalysts include, but are not limited to, copper (I) salts such as cuprous chloride and cuprous iodide, iron (II) salts such as ferrous chloride and ferrous acetate, and metal carbonyls such as iron carbonyl and cobalt carbonyl. Cuprous chloride is preferred. Optionally, any well known co-catalyst useful in catalyzing the addition of halocarbons to olefins may be employed in the reaction. Suitable addition co-catalysts include aliphatic or aromatic amines such as pyridine and diethylamine.

Any inert solvent which can dissolve the catalyst and is miscible with the halocarbon may be used in the reaction. Suitable solvents include, but are not limited to, commercially available low molecular weight nitriles such as acetonitrile and propionitrile, low molecular weight alcohols such as tertiary butanol and isopropanol, and amides such as dimethylformamide. Acetonitrile is preferred because of ease of handling and stability.

The temperature at which the addition reaction is conducted and the period of reaction will depend on the starting material and catalyst used. One of ordinary skill in the art can readily optimize the conditions of the reaction without undue experimentation to get the claimed results but the temperature will generally be in the range of from about 50° to about 150° C. for a period of from about 8–72 hours. When the starting material is one of the preferred compounds and the catalyst is cuprous chloride, the reaction may be conducted at a temperature of from about 80°–150° C. for a period of from about 24 to about 48 hours. Preferably, such a reaction would be conducted at a temperature of from about 125° to about 50° C. for a period of from about 8 to about 30 hours.

Pressure is not critical.

Preferably the reaction is conducted in an apparatus made of corrosion resistant materials such as Teflon and glass.

Preferably, the addition product is recovered from by-products, solvent and catalyst prior to the fluorination reaction to substantially eliminate the production of by-products in the fluorination step. Preferably, the addition product should be about 95% pure. More preferably, the addition product should be about 98% pure. The addition product may be recovered by any means well known in the art such as distillation and extraction. See, for example, Examples 1 and 2 below.

Compounds of the formula $RCX_{a-1}F_bCH_2CH_2X$ where X=Cl or Br, a=2–3, and b=0–1, a+b=3 are the starting material for the fluorination reaction. They may be prepared as discussed above. Preferred starting materials include $CF_3CCl_2CH_2CH_2Cl$, $ClCF_2CFClCH_2CH_2Cl$, and $ClCF_2CF_2CCl_2CH_2CH_2Cl$.

Commercially available hydrogen fluoride (HF) may be used in the fluorination reaction. Preferably, the HF is anhydrous. By "anhydrous" we mean that the HF contains less than about 1 wt. % water and preferably contains less than about 0.5 wt. % water and more preferably contains less than about 0.02 wt. % water. HF suitable for use in the reaction may be purchased from AlliedSignal Inc. of Morristown, N.J.

Any well known vapor phase fluorination catalyst may be used in the fluorination reaction. Suitable fluorination catalysts include the following catalysts and mixtures thereof: metal oxides such as chrome (III) oxide, supported metal oxides such as chrome (III) oxide supported on aluminum oxide or carbon and supported metal halides such as cobalt (II) chloride and nickel (II) chloride supported on carbon, aluminum oxide, aluminum fluoride, or a mixture of such support materials, such as a mixture of $Cr_2O_3$ and $Al_2O_3$. Chrome (III) oxide is preferred due to its level of reactivity and commercial availability. Suitable chrome (III) oxide catalysts may be purchased from Mallinckrodt Specialty Chemicals Co. of St. Louis, Mo.

Over time, the catalyst activity may diminish. In the case where such deactivation is caused by coking, the catalyst may be reactivated, for example, by heating in a stream of air or oxygen. If chrome (III) oxide is the catalyst, following reactivation, the catalyst is preferably pretreated according to the process set forth in Example 3a.

One of ordinary skill in the art can readily optimize the conditions of the reaction without undue experimentation to get the claimed results. Generally, the organics, HF and fluorination catalyst are reacted at a temperature in the range of from about 150° to about 350° C., preferably, from about 200° to about 275° C. and most preferably from about 225° to about 250° C. with a contact time of, for example, about 0.1 to about 240 seconds, preferably from about 1 to about 100 seconds and most preferably from about 5 to about 50 seconds. For purposes of this invention, contact time shall mean the time required for the gaseous reactants to pass through the catalyst bed assuming that the catalyst bed is 100% void.

The molar ratio of HF to organics will depend on the number of nonfluorine halogens in the starting material. Generally, the mole ratio of HF to organics will be from about 1 to about 30 moles HF per mole of nonfluorine halogen present. See Examples 3–6.

Pressure is not critical. Atmospheric and super atmospheric pressure are the most convenient and are therefore preferred. In particular, high reaction pressure is desirable because it makes separation of the HF from HCl easier.

The reaction is preferably conducted in an apparatus made of corrosion resistant material such as Inconel or Monel.

In another embodiment, the invention relates to a process for preparing HFC's comprising:

1) reacting a compound of the formula $RCF_2CH=CH_2$ where R is $C_xCl_yF_z$ and y+z=2x+1 with hydrogen fluoride in the presence of an antimony (V) halide catalyst under conditions sufficient to produce a compound of the formula $RCF_2CH_2CH_2F$ where R is $C_xCl_yF_z$; and y+z=2x+1; and 2) recovering a compound of the formula $RCF_2CH_2CH_2F$ where R is $C_xCl_yF_z$ and y+z=2x+1.

The fluorinated olefin starting material is selected based upon the desired HFC to be produced. For example, if one wanted to produce $CF_3CF_2CH_2CH_2F$, then one would use $CF_3CF_2CH=CH_2$ as the starting material.

Any water in the HF will react with and deactivate the antimony (V) halide catalyst. Therefore, substantially anhydrous HF is preferred. By "substantially anhydrous" we mean that the HF contains less than about 0.05 wt. % water and preferably contains less than about 0.02 wt. % water. However, one of ordinary skill in the art will appreciate that the presence of water in the catalyst can be compensated for by increasing the amount of catalyst used. HF suitable for use in the reaction may be purchased from AlliedSignal Inc. of Morristown, N.J.

Any antimony (V) halide, antimony (V) mixed halide, or mixtures of antimony (V) halide catalysts may be used in the fluorination reaction. Examples of antimony (V) halide catalysts include antimony pentachloride and antimony pentafluoride. Examples of antimony (V) mixed halides include $SbCl_2F_3$ and $SbBr_2Cl_3$. Examples of mixtures of antimony (V) halide catalysts include a mixture of antimony pentachloride and antimony pentafluoride. Antimony pentachloride is preferred because of its low cost and availability.

The temperature at which the organics, hydrogen fluoride and fluorination catalyst are reacted is critical. If the temperature is too low (i.e., <−20° C.), the desired reaction is very slow, but if it is too high (i.e., >20° C.) undesirable side reactions occur, which include the reverse reaction, which reduces yield. Thus, it is preferred to run the reaction at a temperature of from about −20° to about 20° C. A reaction temperature of from about −10° to about 10° C. is more preferred and a reaction temperature of from about −5° to about 5° C. is most preferred.

The stoichiometric molar ratio of HF to organics in the fluorination reaction is 1:1. However, in order to dissolve the catalyst and control reaction temperature, the HF is preferably used in excess i.e., e.g., from about 10–20:1 HF:organics.

Atmospheric or superatmospheric pressure is preferred.

The reaction is preferably conducted in an apparatus made of corrosion resistant material such as Inconel, Monel or Teflon.

EXAMPLE 1

Addition of $CF_3CF_2CCl_3$ to ethylene to produce $CF_3CF_2CCl_2CH_2CH_2Cl$ A Teflon-lined autoclave was charged with 137 g. of cold $CF_3CF_2CCl_3$, 1 g CuI, 20 mL cold $CH_3CN$, and 3 mL pyridine, and evacuated briefly. Ethylene (18.3 g) was then charged and the contents heated to 137° C. for 6 h. After allowing the contents to cool, the volatiles were vented, and the contents were poured into 100 mL 1N HCl. The organic layer was washed with cold water (100 mL) and dried ($CaCl_2$). Distillation provided 87 g of a colorless liquid which was identified spectroscopically as $CF_3CF_2CCl_2CH_2CH_2Cl$ (bp 71°–73° C. at 75–6 mm Hg). $^1H$ NMR: equal intensity triplets at δ3.93 and 2.82; $^{19}F$ NMR: −77.3 (3 F) and −117.5 (2 F) ppm; IR: strong bands at 1225, 1185, 1160 cm$^{-1}$. Gas chromatography determined that the product was 99.6% pure.

EXAMPLE 2

Addition of $CF_3CCl_3$ to ethylene to produce $CF_3CCl_2CH_2CH_2Cl$

A 600 mL stirred Monel autoclave was charged with 30 mL $CH_3CN$, 3 mL pyridine, 1 g CuI, and 199.6 $CF_3CCl_3$. The contents were cooled to −29° C., the autoclave briefly evacuated, and charged with 24.4 g ethylene. The contents were then heated to 135°–145° C. for 22 h. After cooling the contents, the volatiles (unreacted ethylene) were vented. The residue was diluted with 300 mL water, and extracted with 50 mL $CH_2Cl_2$. The organic layer was then washed twice with 50 mL 5% aqueous HCl, twice with 50 mL 5% NaOH, twice with 50 mL water and finally dried ($CaCl_2$). Distillation at 145 mm Hg gave 80 g (58% yield) of a colorless liquid which was identified spectroscopically as $CF_3CCl_2CH_2CH_2Cl$ (bp 102°–103° C.). $^1H$ NMR: equal intensity triplets at δ3.9 and 2.77; $^{19}F$ NMR: −81 (s) ppm; IR: strong bands characteristic of $CF_3CCl_2CH_2$— grouping at 1255, 1210, and 1180 cm$^{-1}$. Gas chromatography determined that the product was 99% pure. $CF_3CCl_2CH_2CH_2Cl$ has utility as an intermediate in the preparation of fluroinated olefins of the invention which may be used to prepare hydrofluorocarbons. See Example 3 below.

EXAMPLE 3

Vapor phase fluorination of $CF_3CCl_2CH_2CH_2Cl$ to produce $CF_3F_2CH=CH_2$ (a) Catalyst Pretreatment.

While maintaining a nitrogen flow of 350 mL/min through a 1 inch pipe reactor, pelletized chrome oxide ($Cr_2O_3$), (available from Mallinckrodt Specialty Chemicals Co., St. Louis, Mo.) was heated to 350° C. at a rate of 50 C/h, maintained at 350° C. for 8 h, then cooled to 200° C. at a rate of 40 C/h. Liquid hydrogen fluoride was then metered in at a rate to keep the temperature below 250° C. (about 0.8 cc/min). After the exotherm had moved through the catalyst bed, the temperature was again increased to 350° C. at a rate of 50 C/h, and held at 350° C. for 2 h. Finally, the temperature was decreased to 250° C. at a rate of 50 C/h.

(b) Fluorination Reaction.

The pretreated catalyst (150 cc) was heated to 250° C. in the reactor while passing HF into the reactor at 1.4 mL/min at an operating pressure of 50 psig. The organic, $CF_3CCl_2CH_2CH_2Cl$, was then fed at 0.7 g/min (contact time 10 sec). Gas chromatographic analysis of the reactor effluent indicated an 83% conversion of starting material. The products, which were collected in a −78° C. cold trap and identified by GC-MS, included $CF_3CF_2CH=CH_2$ (23.4%), $C_4H_3ClF_4$ isomers (5.5%), $CF_3CF_2CH_2CH_2Cl$ (4.4%), $CF_3CCl_2CH_2CH_2F$ (2.1%), and $C_4H_3Cl_2F_3$ isomers (62.9%). The desired olefin, $CF_3F_2CH=CH_2$ (bp 3°–6° C.) was readily recovered in high purity from the crude product by bulb-to-bulb distillation. The $C_4H_3Cl_2F_3$ isomers were later separated via distillation using a three-foot packed column and identified as follows: fraction boiling at 95°–101° C. consisted of 10% $CF_3CCl_2CH_2CH_2F$ and $CF_3CCl=CHCH_2Cl$ (86 and 4% respectively); fraction boiling at 101° C. consisted of $CF_3CCl_2CH_2CH_2F$ (3%) and a mixture of cis- and trans-$CF_3CCl=CHCH_2Cl$ (92 and 5%). $^1H$ NMR for $CF_3CCl_2CH_2CH_2F$: δ2.74 (dt, C$\underline{H}_2CH_2F$, JH-F=18.6 Hz, JH-H=6.3 Hz) and 4.83 (dt, $CH_2C\underline{H}_2F$, JH-F=46.2 Hz, JH-H=6.3 Hz); $^{19}F$ NMR: −80.7 and −222.4 ppm. $^1H$ NMR for $CF_3CCl=CHCH_2Cl$: δ6.61 (=C$\underline{H}$, JH-H=7.2 Hz, JH-F=1.0 Hz) and 4.24 (C$\underline{H}_2Cl$, JH-H=7.2 Hz, JH-F=0.5 Hz); $^{19}F$ NMR: −70.6 ppm. Cis- and trans-$CF_3CCl=CHCH_2Cl$ are useful as starting materials for the manufacture of hydrofluorocarbons which may application as solvents among other things.

(c) Recycle of underfluorinated (chlorinated by-products) materials.

The by-products recovered above, specifically a mixture containing 7.5% $CF_3CCl_2CH_2CH_2F$ and 92.3% cis- and trans-$CF_3CCl=CHCH_2Cl$ were placed into the reactor and then passed over 150 cc of the catalyst at 50 psig and a temperature of 225° C. HF feed rate was 1.4 cc/min, while the organic feed rate was 0.7 g/min corresponding to a contact time of about 10 sec. Gas chromatographic analysis of the reactor effluent indicated that it was comprised of 79% $CF_3CF_2CH=CH_2$. This indicated to us that $CF_3CCl=CHCH_2Cl$ must be an intermediate in the vapor phase fluorination of $CF_3CCl_2CH_2CH_2Cl$ to $CF_3CF_2CH=CH_2$. Were it otherwise, the yield of $CF_3CF_2CH=CH_2$ would have been much lower, reflecting the fluorination of only 7.5% $CF_3CCl_2CH_2CH_2F$.

EXAMPLES 4–6

Vapor phase fluorination of $CF_3CCl_2CH_2CH_2Cl$ to produce $CF_3F_2CH=CH_2$ The experiment reported in Example 3 was repeated using the temperatures, pressures and contact times reported in Table 1 below.

TABLE I

|  | 4 | 5 | 6 |
|---|---|---|---|
| Pressure (psig) | 100 | 200 | 200 |
| Temperature (C.) | 200 | 225 | 250 |
| Contact time (s) | 18 | 32 | 30 |
| Conversion (%) | 60 | 73 | 79 |
| Selectivity (%) for |  |  |  |
| $CF_3CF_2CH_2CH_2F$ | 1 | 1 | 1 |
| $CF_3CF_2CH=CH_2$ | 22.1 | 18.1 | 23.4 |
| $CF_3CCl=CHCH_2Cl$ | 74.2 | 78.1 | 72.5 |
| Other | 2.7 | 2.8 | 3.1 |

These Examples show that there is a range of operating conditions that give useful quantities of a desired olefin.

EXAMPLE 7

Hydrofluorination of $CF_3CF_2CH=CH_2$ to produce $CF_3CF_2CH_2CH_2F$

A stirred PTFE reactor, connected to a $CaSO_4$ drying tube, a caustic scrubber and a −78° C. cold trap, was charged with 3.2 g $SbCl_5$ and 55.0 g HF at 0° C. Over a period of 4.75 h, 29.0 g $CF_3CF_2CH=CH_2$ was bubbled into the HF solution. After stirring for an additional hour at 0° C., the dark red reaction mixture was poured cautiously into ice-cold 5% aqueous KOH. The lower light brown organic phase (18.2 g) was analyzed using gas chromotography and found to contain 70.0% $CF_3CF_2CH_2CH_2F$, 14.3% $CF_3CF_2CH_2CHCl$, and 15.7% of higher boiling materials (including 8-carbon compounds). Distillation of a larger sample of crude $CF_3CF_2CH_2CH_2F$ provided pure material having the following properties: bp 44°–45° C., $^1H$ NMR: δ4.69 (dt, J=46.4 and 5.6 Hz, C$\underline{H}$+b 2F) and 2.45 (m, CF2C$\underline{H}$2); $^{19}F$ NMR: −87.1 (3 F), −118.6 (2 F, dt, J=17.8 and 6.4 Hz), and −223.1 (1 F) ppm.

The 8-carbon compounds produced as by-products in this reaction were identified by GC-MS as primarily isomeric olefins (2:1 ratio) of the molecular formula C8H6F10. The major isomer was identified by NMR analysis as $CH_2=C(CF_2CF_3)CH(CH_3)(CF_2CF_3)$, while the minor isomer was $CF_3CF_2CH_2CH=C(CH_3)(CF_2CF_3)$. $^1H$ NMR for the major isomer: δ1.3 (d, C$\underline{H}$3, 3JH-H=7 Hz), 3.0 (m, —C$\underline{H}$(CH_3), 5.8 (dt, =C$\underline{H}$H, J=16 and 11 Hz), and 6.38 (dd, =CH$\underline{H}$, J=16 and 9 Hz); $^{19}F$ NMR: −83.7 (s, 3 F), −87.1 (s, 3 F), −117.8 (d, 1 F), −118.0 (d, 1 F, J=11 Hz), −121.0 (dd, 1 F, J =271 and 11 Hz), and −124.6 (dd, 1 F, J=271 and 18 Hz) ppm. $^1H$ NMR for the minor isomer: δ1.85 (s, 3H), 3.0 (m, 2H), and 6.15 (t, 1H, J=7 Hz); $^{19}F$ NMR: −85.5 (s, 3 F), −86.9 (s, 3 F), −188.2 (t, 2 F, J=16 Hz), and −119.0 (s, 2 F) ppm.

Comparative Example 1

Fluorination of $CF_3CCl_2CH_2CH_2Cl$ with HF/$SbCl_5$

A monel autoclave was charged with 5.6 g $SbCl_5$, 29.8 HF, and 54.2 g $CF_3CCl_2CH_2CH_2Cl$. The contents were stirred and heated to 175° C. for 14 h. The contents were vented into a caustic scrubber, followed by a −78° C. cold trap. Product was recovered from the cold trap and the scrubber and analyzed using gas chromatography. Product recovered from the scrubber was identified as 40.8 g of starting material (98% purity). The 2.2 g of product from the cold trap also identified as primarily starting material.

Comparative Example 2

Fluorination of $CF_3CCl_2CH_2CH_2Cl$ with HF/$SbCl_5$ at higher temperature

The experiment outlined in Comparative Example 1 was repeated using the following materials and reaction conditions: 9.7 g $SbCl_5$, 36.2 g HF, 32.3 g $CF_3CCl_2CH_2CH_2Cl$ were mixed, stirred and heated at 225° C. for 14 h. Results similar to those reported in Comparative Example 1 were obtained; the scrubber contained 97% starting material, while the cold trap contained a small amount of $CF_3CCl_2CH=CH_2$ and a $C_4H_4F_4Cl_2$ isomer. Thus, unlike $CCl_3CH_2CH_2Cl$ which fluorinated readily to $CF_3CH_2CH_2Cl$ with HF and antimony pentachloride at modest temperature (85° C.) (U.S. Pat. No. 4,078,007), the $CCl_2$ group in $CF_3CCl_2CH_2CH_2Cl$ was resistant to fluorination even at elevated temperature (>175° C.).

Comparative Example 3

Hydrofluorination of $CF_3CF_2CH=CH_2$

A monel autoclave was charged with 6.5 g $SbF_5$, 30 g HF, and 43.8 g $CF_3CF_2CH=CH_2$. The mixture was heated to 105° C. for 12 h. Venting the reaction mixture into a caustic scrubber, followed by cold traps, gave 33 g of product mixture, while the autoclave residue consisted of black liquid and solid. Gas chromatographic analysis of the 33 g of organic product indicated that it contained 54% $CF_3CF_3CH_2CH_2F$, 33% of a $C_8H_6F_{10}$ isomer, and 5% starting material.

Comparative Example 4

Hydrofluorination of $CF_3CF_2CH=CH_2$

The experiment outlined in Comparative Example 3 was repeated using the following materials and reaction conditions: 3.9 g $SnCl_4$, 20 g HF, and 43.8 g $CF_3CF_2CH=CH_2$ were mixed together and heated to 98°–106° C. for 5 h to give 40 g of liquid product which gas chromatographic analysis indicated consisted of 94% starting material.

Comparative Example 5

Hydrofluorination of $CF_3CF_2CH=CH_2$

The experiment outlined in Comparative Example 3 was repeated using the following materials and reaction conditions: 8.5 g $TaF_5$, 40.3 g HF, and 47.4 g $CF_3CF_2CH=CH_2$ were mixed together and heated to 108° C. for 17.5 h to give 44.3 g of product which gas chromatographic analysis indicated consisted of 29% starting material, 1% $CF_3CF_2CH_2CH_2F$, 20% $C_8H_6F_{10}$, and 46% polymeric material.

These comparative examples show that use of Lewis acid catalysts and elevated temperatures (the teachings of Henne et al., discussed above) result in either little reaction or unacceptably large quantities of byproducts, such as higher boiling materials.

Comparative Examples 6–8

Hydrofluorination of $CF_3CF_2CH=CH_2$ at low temperatures with catalysts other than $SbCl_5$ The experiment outlined in Example 7 above was repeated using each of the following Lewis acid catalysts: $TiCl_4$, $SnCl_4$, and $BF_3$. In each case, none of the desired $CF_3CF_2CH_2CH_2F$ product was obtained and virtually no reaction occurred.

We claim:

1. A process for preparing a hydrofluorocarbon comprising:

a) reacting a compound of the formula $RCF_2CH=CH_2$ where R is $C_xCl_yF_z$ and $y+z=2x+1$ with hydrogen fluoride in the presence of an antimony (V) halide catalyst under conditions sufficient to produce a compound of the formula $RCF_2CH_2CH_2F$ where R is $C_xCl_yF_z$ and $y+z=2x+1$; and b) recovering a compound of the formula $RCF_2CH_2CH_2F$ where R is $C_xCl_yF_z$ and; $y+z=2x+1$.

2. The process of claim 1 wherein said compound of the formula $RCF_2CH=CH_2$ where R is $C_xCl_yF_z$ and $y+z=2x+1$ is $CF_3CF_2CH=CH_2$.

3. The process of claim 1 wherein said hydrogen fluoride is anhydrous.

4. The process of claim 2 wherein said hydrogen fluoride is anhydrous.

5. The process of claim 1 wherein said antimony (V) halide is selected from the group consisting of antimony (V) halides, antimony mixed halides or mixtures of antimony (V) halides.

6. The process of claim 4 wherein said antimony (V) halide is antimony (V) pentachloride.

7. The process of claim 1 wherein the stoichiometric molar ratio of $HF:RCF_2CH=CH_2$ where R is $C_xCl_yF_z$ and $y+z=2x+1$ is from about 10–20:1.

8. The process of claim 6 wherein the stoichiometric molar ratio of $HF:RCF_2CH=CH_2$ where R is $C_xCl_yF_z$ and $y+z=2x+1$ is from about 10–20:1.

9. The process of claim 1 wherein said conditions sufficient to produce a compound of the formula $RCF_2CH_2CH_2F$ where R is $C_xCl_yF_z$ and $y+z=2x+1$ are a temperature of from about −20° to about 20° C.

10. The process of claim 8 wherein said conditions sufficient to produce a compound of the formula $RCF_2CH_2CH_2F$ where R is $C_xCl_yF_z$ and $y+z=2x+1$ are a temperature of from about −5° to about 5° C.

* * * * *